United States Patent [19]
Grieshaber et al.

[11] Patent Number: 5,360,398
[45] Date of Patent: Nov. 1, 1994

[54] OPHTHALMOLOGICAL ASPIRATION AND IRRIGATION SYSTEM

[75] Inventors: Hans R. Grieshaber; Rudolf Demmerle; Urs Vogel, all of Schaffhausen, Switzerland

[73] Assignee: Grieshaber & Co. AG Schaffhausen, Switzerland

[21] Appl. No.: 147,926

[22] Filed: Nov. 4, 1993

[30] Foreign Application Priority Data

Nov. 6, 1992 [CH] Switzerland .................. 03448/92
Sep. 23, 1993 [CH] Switzerland .................. 02872/93

[51] Int. Cl.⁵ .................. A61M 1/00; A61M 31/00
[52] U.S. Cl. .................. 604/30; 604/33; 604/67
[58] Field of Search .................. 604/23, 26, 27, 28, 604/30–33, 67, 118, 119

[56] References Cited

U.S. PATENT DOCUMENTS

| | | | |
|---|---|---|---|
| 3,589,363 | 6/1971 | Banko | 604/27 |
| 3,693,613 | 9/1972 | Kelman | 604/31 |
| 4,117,843 | 10/1978 | Banko | 604/31 |
| 4,184,510 | 1/1980 | Murry et al. | 604/30 |
| 4,551,131 | 11/1985 | Miles et al. | 604/31 |
| 4,832,685 | 5/1989 | Haines | 604/30 |
| 4,900,301 | 2/1990 | Morris et al. | 604/23 |
| 5,242,404 | 9/1993 | Conley et al. | 604/30 |

*Primary Examiner*—John D. Yasko
*Assistant Examiner*—Frank Wilkens, III
*Attorney, Agent, or Firm*—Henry M. Feiereisen

[57] ABSTRACT

An aspiration and irrigation system, in particular for performing surgical operations on an eye of a living being to maintain the intraocular pressure, includes a pressure unit for supplying gaseous fluid to the eye via a first fluid passageway and communicating with an infusion unit comprised of successively arranged first and second infusion bottles, both containing a liquid fluid. An irrigation unit is connected with the second infusion bottle for conducting liquid fluid from said second infusion bottle to the eye via a second fluid passageway; with the liquid fluid in the second infusion bottle being pressurized by gaseous fluid supplied from the pressure unit. A multiport valve selectively controls the flow between the first and second fluid passageways to the eye. Tissue and/or gaseous and liquid fluids are removed from the eye by an aspiration unit.

15 Claims, 3 Drawing Sheets ated body of a living being to maintain the intraocular pressure, and in particular relates to an aspiration and irrigation system of the type having a pressure unit for supplying a gaseous fluid, an irrigation unit which is in communication with an infusion bottle with dropper for conducting liquid fluid to the eye, and with an aspiration unit for removing tissue and/or fluid from the eye.

OPHTHALMOLOGICAL ASPIRATION AND IRRIGATION SYSTEM

BACKGROUND OF THE INVENTION

The present invention refers to an aspiration and irrigation system, especially for performing surgical operations on the eye of a living being to maintain the intraocular pressure, and in particular relates to an aspiration and irrigation system of the type having a pressure unit for supplying a gaseous fluid, an irrigation unit which is in communication with an infusion bottle with dropper for conducting liquid fluid to the eye, and with an aspiration unit for removing tissue and/or fluid from the eye.

U.S. Pat. No. 4,935,005 discloses an ophthalmic fluid flow control system for use with a surgical irrigation and aspiration instrument which is connected with an ultrasonic device and a peristaltic pump. The ultrasonic device is supplied with a liquid irrigation fluid from a container via a fluid conduit including a first valve and a successively arranged control valve in order to attain an ophthalmic irrigation. Subsequently, tissue-containing fluid is removed from the surgical site by the peristaltic pump via an aspiration conduit, which is connected to the ultrasonic device and to a pressure-sensitive transducer, for discharge into a collector. The transducer monitors the suction capacity of the peristaltic pump and thus senses a vacuum rise in the aspiration conduit so that the supply of irrigation fluid can be interrupted when e.g. the selected suction capacity is exceeded through blockage caused by tissue-enriched fluid.

U.S. Pat. No. 4,900,301 discloses an ocular perfusion device in communication with an ophthalmological irrigation and aspiration system in which a pressure-generating pump supplies e.g. an air/gas mixture at a certain output pressure to the infusion instrument via a first conduit of a dropper which is provided with a liquid container adjustable to the level of the eye and via a second conduit which is connected to a multiport valve. A third conduit is linked to the multiport valve for supplying infusion fluid from the dropper to the infusion instrument.

Common to these prior art systems is the drawback that the intraocular pressure is determined by the infusion level of the container which is arranged e.g. on a stand or the like, or on the infusion level of the dropper. In the event, the intraocular pressure should be modified because of e.g. hemorrhaging during a surgical procedure, the change can be accomplished only through a cumbersome and instinctive adjustment of the height of the container or the dropper.

SUMMARY OF THE INVENTION

It is an object of the present invention to provide an improved aspiration and irrigation system obviating the afore-stated drawbacks.

In particular, it is an object of the present invention to provide an improved aspiration and irrigation system which allows a rapid and precise control of the intraocular pressure with gaseous or liquid fluids during surgical procedure and enables a controlled pressure increase in circumstances such as hemorrhaging or the like.

These objects and others which will become apparent hereinafter are attained in accordance with the present invention by placing in the liquid fluid supply line between the infusion bottle and the irrigation unit a second infusion bottle which is in communication with the pressure unit for introduction of gaseous fluid to pressurize the liquid fluid in the second infusion bottle, and by connecting the supply lines from the pressure unit and the irrigation unit to a multiport valve for selective control of the intraocular pressure through gaseous and liquid fluids.

By pressurizing the liquid fluid in the second infusion bottle through gaseous fluid from the pressure unit, the liquid fluid as well as the gaseous fluid can be infused into the eye at precisely controlled pressure and dosage. The pressure is sensed by a pressure gage and suitably displayed on a display panel of the ophthalmological device for easy and rapid adjustment.

BRIEF DESCRIPTION OF THE DRAWING

The above and other objects, features and advantages of the present invention will now be described in more detail with reference to the accompanying drawing in which.

DETAILED DESCRIPTION OF PREFERRED EMBODIMENTS

Figure 1:
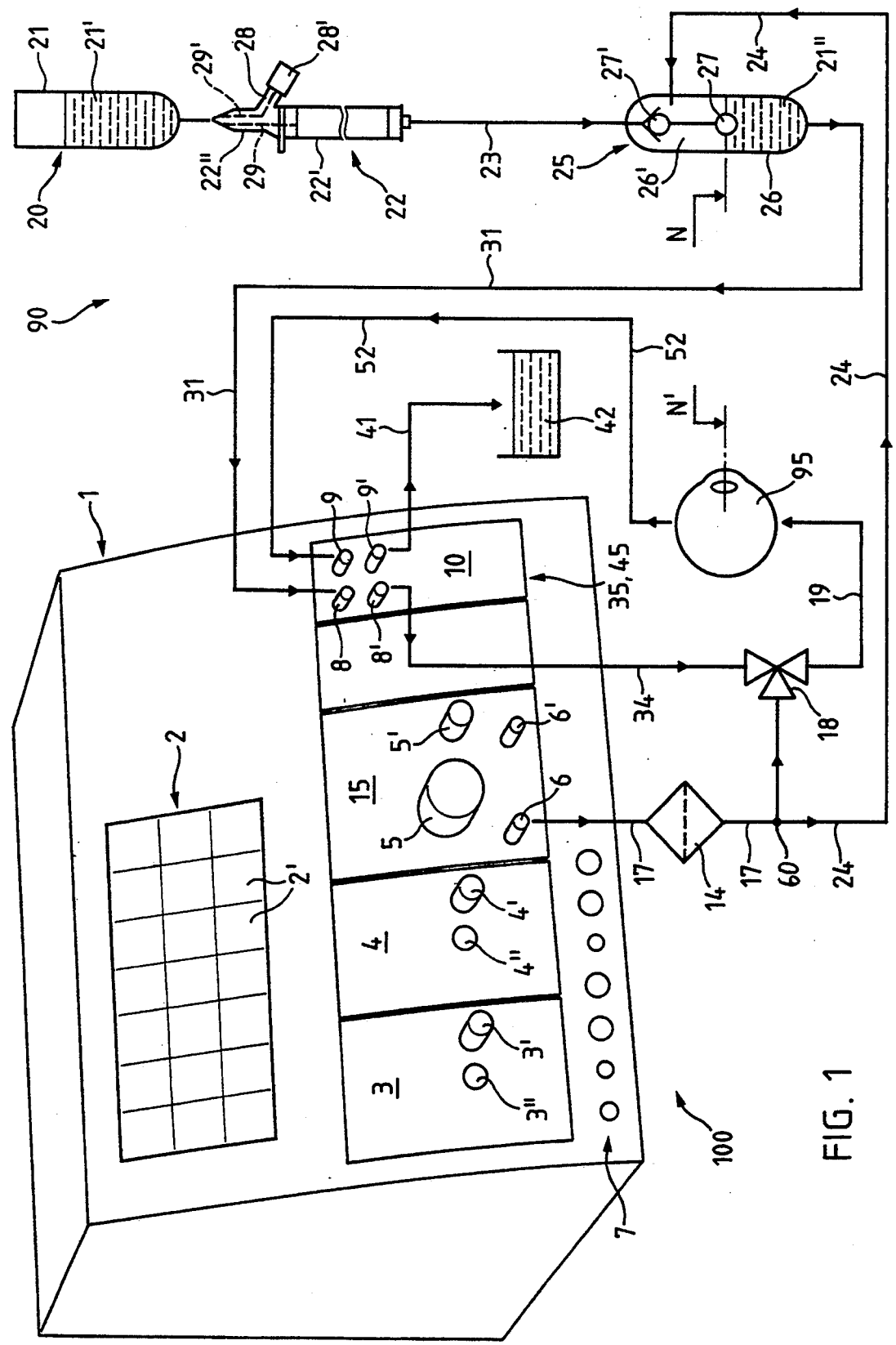
FIG. 1 is a simplified flow diagram to explain the control principle of an aspiration and irrigation system which is part of an ophthalmologic device illustrated in perspective view.

Referring now to the drawing, and in particular to FIG. 1, there is shown a schematic illustration of an aspiration and irrigation system according to the present invention which is part of an ophthalmologic device illustrated in perspective view and generally designated by reference numeral 100. The ophthalmologic device 100 is used for microsurgical operations on an eye 95 of a living being and includes a housing 1 with a front console comprised of several side-by-side compartments for receiving exchangeable functional units 3, 4, 15, 35, 45 which are designed in form of plug-in cassettes 10 to serve particular surgical procedures. Below the compartments, the front face of the housing 1 is further provided with a multipoint connector 7 for enabling attachment of additional surgical instruments.

Both functional units 3, 4 constitute lighting units which illuminate the surgical site of the eye. The structure of such lighting units 3, 4 is generally known and may include an optical conductor with a light source on one end and an adapter on the other end for attachment to complementary jacks 3" and/or 4" on the front console of housing 1. During surgical procedure, the light intensity of the lighting units 3, 4 can be continuously controlled by adjustment knobs 3' and 4'. The optical conductor together with the light source and adapter as well as much other additional apparatus such as electric circuits do not form part of the present invention and thus have been omitted from the drawing for sake of simplicity.

As further indicated in FIG. 1 and described in more detail with reference to FIG. 2, the functional units 15, 35, 45 are operatively connected with an aspiration and irrigation instrument which is generally designated by reference numeral 90. The aspiration and irrigation instrument 90, illustrated in FIG. 1 by way of a simplified flow diagram to explain the general control principle, is provided for simultaneous removal of fluid and/or tissue from the eye and replacement with fluid or gas.

Arranged above the compartments, the console of the housing 1 is further provided with a display panel 2 which e.g. is subdivided into separate LCD sections 2' for indicating and controlling certain operations. The display panel 2 is part of a not shown computerized control system to provide the user with certain informations of the ophthalmologic device 100, as well as to enable the user to manipulate procedures by touching respective sections 2' of the panel 2 and thus to initiate the selected program which is then illuminated.

The functional unit 15 which is situated next to the lighting unit 4 is a pressure gas supply unit for feeding a pressure gas such as compressed air to the surgical site and forms part of the aspiration and irrigation instrument 90. The functional unit or pressure unit 15 includes a connector 6 for attachment of a tube 17 and an adjustment knob 5 for controlling, preferably continuously, the supply of compressed air to the surgical site for maintaining the required intraocular pressure of the eye. Preferably integrated within the housing 1 and operatively connected to the pressure unit 15 is a visco-injection device (not shown) which includes a connector 6' for attachment of a tube (not shown) and an adjustment knob 5' for control purposes.

The compartment next to the pressure unit receives a cassette system which contains the functional units 35 and 45, representing the irrigation unit 35 and the aspiration unit 45 and includes spaced connectors 8, 8' and 9, 9' for a purpose to be described hereinafter with reference to FIG. 2.

As shown in FIG. 1, the aspiration and irrigation instrument 90 is further provided with an infusion unit 30 which is operatively connected to the pressure unit 15, the irrigation unit 35 and the aspiration unit 45 of the ophthalmological device 100 and essentially includes a pair of successively arranged first and second infusion instruments 20, 25 with interposed dropper 22.

The first infusion instrument 20 includes an infusion bottle 21 which contains a saline solution 21' and is connected via the dropper 22 with an infusion bottle 26 of the second infusion instrument 25 by a conduit 23. The infusion bottle 26 contains a liquid fluid such as saline solution 21" which exits the infusion bottle 26 through tube 31 that is attached to connector 8 of the irrigation unit 35. The level N of the saline solution 21" is monitored by a float valve 27 which interacts with a control valve 27' so as to keep the level N constant and maintain it in alignment with the position-dependent level N' of the eye 95. It is of importance that during a surgical operation, both levels N and N' are at least approximately in alignment with each other, as indicated in FIG. 1.

The infusion bottle 26 communicates with the pressure unit 15 via a tube 24 which enters with one end the space 26' of the infusion bottle 26 above the liquid level N and is connected with its other end to a connection point in form of a T-piece 32 for communication with the tube 17 which is attached to the connector 6 of the pressure unit 15 via a filter 14 for sterilization of the pressure gas. Thus, sterilized compressed air is admitted into the space 26' of the infusion bottle 26 to pressurize the saline solution 21".

Attached to the connector 8' of the irrigation unit 35 is one end of a tube 34 which is connected with its other end to a multiport valve (three-way valve) 18 from which a tube 19 leads to the eye 95. The connection point 32 at which the tubes 17 and 24 are united is also linked to the multiport valve 18. Thus, by suitably controlling the multiport valve 18, the eye 95 can be irrigated with strerilized compressed air from the pressure unit 15 via tubes 17 and 19 or with liquid fluid such as saline solution 21" from the irrigation unit 35 via the tubes 34 and 19. Since pressure gas is also admitted to the infusion bottle 26 at a pressure set by the pressure unit 15, saline solution 21" can be supplied at a predetermined and continuously controllable pressure for maintainng the intraocular pressure (IOP).

Persons skilled in the art will understand that tube 24 may also be directly connected to the pressure unit 15 via a not shown connector so that sterilized compressed air can be directly admitted to the infusion bottle 26.

Removal of fluid and tissue during a surgical operation from the eye is accomplished by the aspiration unit 45 which is provided with a suitable vacuum source and has an external connector 9 for receiving one end of a tube 52, the other end of which enters the eye 95. By applying a suitable vacuum, the fluid or tissue is drawn from the eye 95 and discharged to a waste container 42 via a tube 41 which is attached to a connector 9' of the aspiration unit 45. Certainly, the waste container 42 may also be incorporated within the housing 1 of the ophthalmological device 100.

Figure 2:
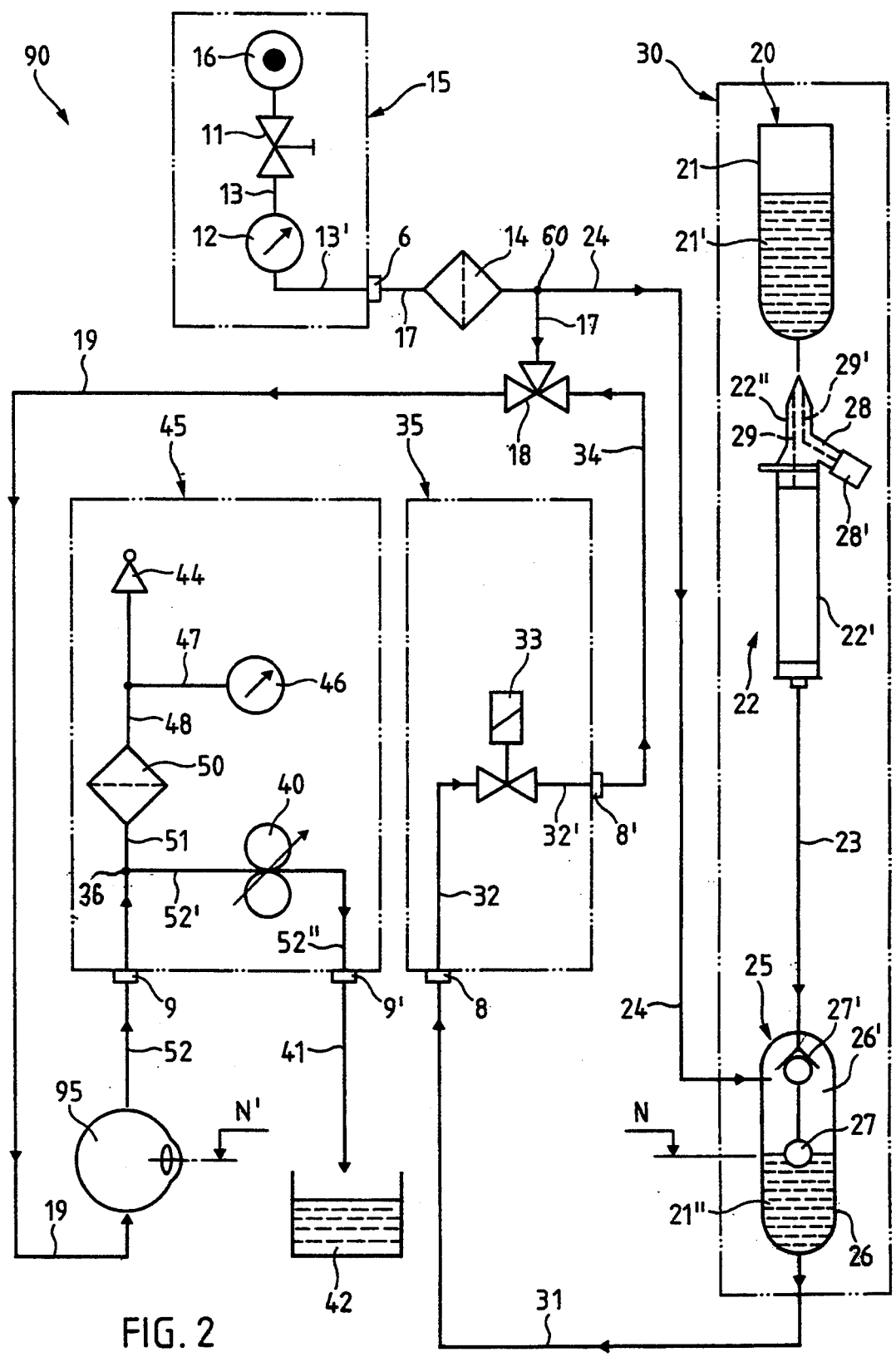
FIG. 2 is a complete flow diagram of the aspiration and irrigation system of FIG. 1, including the relevant control devices.

Turning now to FIG. 2, there is shown a complete flow diagram of the aspiration and irrigation system 90, with more detailed illustration of the relevant elements of the individual functional units 15, 30, 35 and 45.

The pressure unit 15 includes a pressure gas source 16 and a control valve 11 for regulating the flow of pressure gas from the source 16 through a tube 13. A pressure gage measures the pressure in tube 13 which is continued by a tube 13' leading to the connector 6 of the pressure unit 15. The pressure as set by the control valve 11 is detected by the pressure gage 12 and the value commensurate with the pressure is displayed by one of the display sections 2'. If necessary, the pressure can be adjusted, e.g. continuously, by adjustment knob 5.

Tube 17 leads from the connector 6 of the pressure unit 15 via filter 14 to the connection point 32 where the gas flow is divided into two partial flows, with one partial gas flow being conducted through tube 24 into the space 26' of the second infusion bottle 26 and with the other partial gas flow flowing via tube 17 to the multiport valve 18.

The dropper 22 of the infusion unit 30 may be of any suitable design and is directly attached to the infusion bottle 21 via a tubular connecting piece 22" and includes a reservoir 22' which is in communication with the infusion bottle 26 via the tube 23. Branching off laterally from the connecting piece 22" is a conduit 28 for attachment of a filter 28'. The reservoir 22' and the infusion bottle 21 are connected with each other via a fluid passageway 29 which extends axially through the connecting piece 22". The tube 28 accommodates a fluid passageway 29' which extends through the connecting piece 22" and into the infusion bottle 21 so that during flow of saline solution 21' to the infusion bottle 26, sterilized air is drawn simultaneously via the filter 28' into the infusion bottle 21.

During a drop of the fluid level N in the infusion bottle 26, an underpressure is generated in the dropper 22. When the fluid level N' falls below a predetermined minimum level, the float valve 27 opens the valve 27', effecting a flow of saline solution 21' from the infusion bottle 21 via the dropper 22 and tube 23 into the infusion bottle 26 while air sterilized by filter 28' is drawn through passageway 29' into the infusion bottle 21 at the same time. As soon as the saline solution 21" in the infusion bottle 26 reaches the predetermined fluid level N, valve 27' closes again.

It will be appreciated by persons skilled in the art that the replenishing of liquid fluid 21' in the infusion bottle 26 as well as the opening and closing of the valve 27' is carried out automatically and is attained under absolutely sterilized conditions.

Saline solution 21" is drawn from the infusion bottle 26 through tube 31 and into the irrigation unit 35 via connector 8. The irrigation unit 35 includes an interrupter element 33 which is linked to both connectors 8, 8' via respective tubes 32, 32'. Preferably, the interrupter element 33 is a controllable solenoid valve with a not shown squeeze element by which the elastic tubes 32, 32' can be clamped or opened to control the supply of liquid fluid 21" to the eye 95. Attached to the connector 8' is the tube 34 which leads via the multiport valve 18 and tube 19 to the eye 95. Fluid and tissue is removed from the eye 95 via the tube 52 which is attached to the connector 9 of the aspiration unit 45.

The aspiration unit 45 includes a pump, e.g. a peristaltic pump 40 which is connected by conduit 52' via connection point 36 to connector 9 and via conduit 52" with connector 9' so as to generate a suction in tube 52 while forcing removed tissue through conduit 52" and the tube 41 into the waste container 42. Gaseous fluid withdrawn from the eye 95 by the peristaltic pump 40 may be discharged through a conduit 51, a filter 50 and a conduit 48 via a ventilating valve 44. A pressure gage 46 measures via conduit 47 the pressure in conduit 48.

Figure 3:
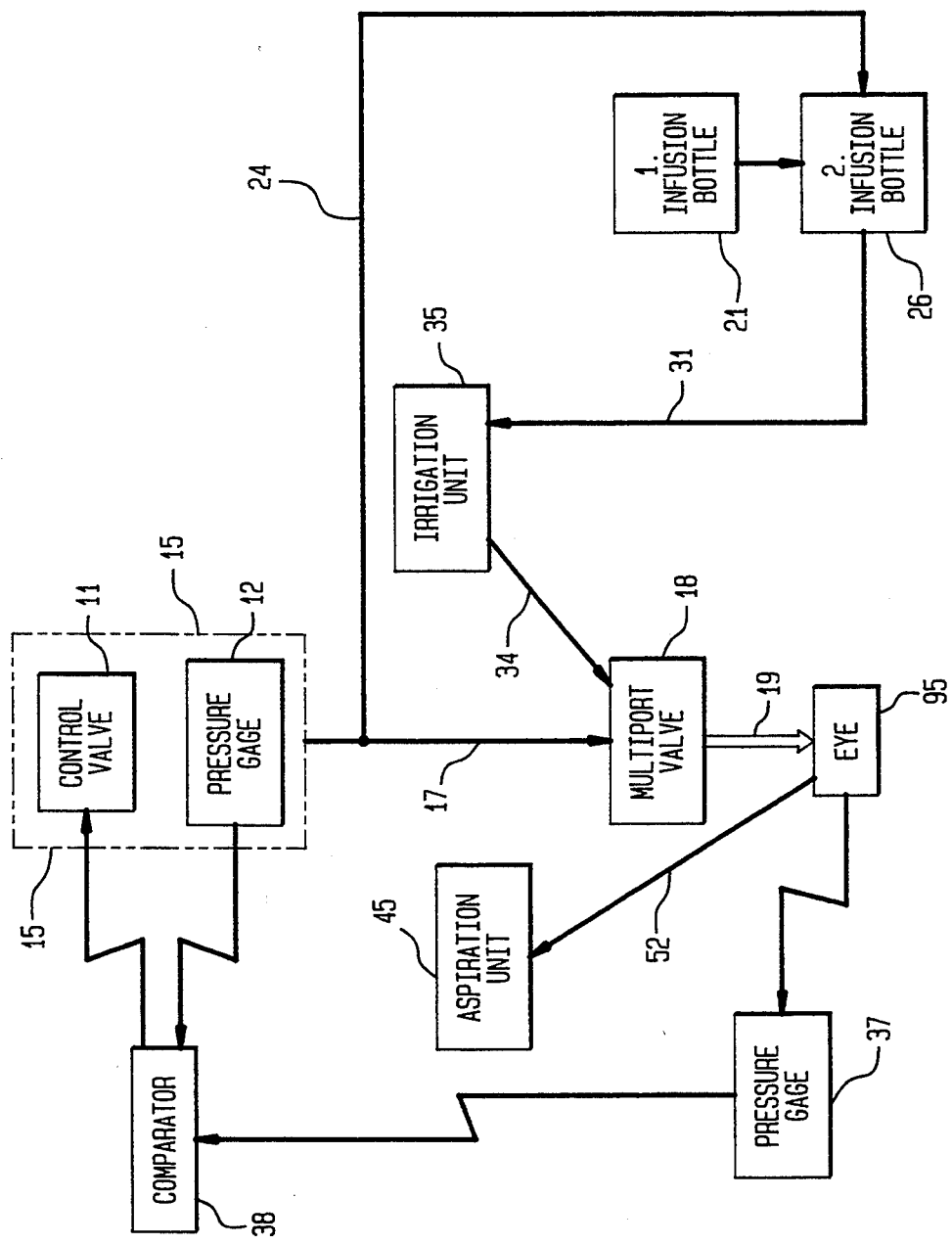
FIG. 3 is a simplified block diagram illustrating a general overview of the aspiration and irrigation system of FIG. 1.

Turning now to FIG. 3, there is shown a simplified block diagram illustrating a principal overview of the aspiration and irrigation system 90 of FIG. 1. Tubes 17 and 19 define a first supply line through which sterilized gaseous fluid from the pressure unit 15 is conducted to the eye 95. Tubes 31 and 34 which are connected to the first supply line form a second supply line for conducting liquid fluid to the eye 95. Tube 24 which communicates with tube 17 via filter 14 forms a third supply line by which sterilized, gaseous fluid is admitted into the infusion bottle 26 to pressurize the contained liquid fluid 21" and thus to allow precise control of liquid fluid 21" being conducted to the eye 95.

By suitably controlling the multiport valve 18, the eye 95 can thus be supplied at controlled pressure with either sterilized gaseous fluid from the pressure unit 15 via the first supply line 17, 19 or with sterilized liquid fluid from the infusion bottle 26 via the second supply line 31, 34, 19, with the pressure being regulated by the gaseous fluid building up in the infusion bottle 26 and set by the pressure unit 15.

Tube 52 connecting the eye 95 with the aspiration unit 45 defines a first discharge line while tube 41 connecting the aspiration unit 44 with the waste container 42 defines a second discharge line.

Suitably, all tubes and conduits for gaseous and liquid fluids are made in form of flexible hoses, preferably of transparent plastic material or the like. Both infusion bottles 21 and 26 of the infusion unit 30 as well as the dropper 22 should also be made of transparent plastic material.

As further shown in FIG. 3 by way of example, a preferred embodiment of the present invention includes a pressure gage 37 by which the momentary intraocular pressure of the eye is permanently monitored and suitably indicated on the display panel 2 of the ophthalmological device 100. The actually sensed pressure is fed to a comparator 38 of the pressure unit 15 for comparison with the selected pressure and indication on the display panel 2. Thus, the pressure of the supplied gaseous or liquid fluid can be adjusted i.e. increased or decreased by setting the desired pressure on the display panel 2 (through slight finger pressure) to suitably adjust the control valve 11.

In the non-limiting embodiment of the present invention, the individual functional units 3, 4, 15, 35 and 45 are provided in form of cassette systems which are slidable into the respective compartments of the housing 1 of the ophthalmological device 100. Persons skilled in the art will understand, however, that these individual functional units may however also be fitted in separate housings and respectively positioned.

While the invention has been illustrated and described as embodied in an ophthalmological aspiration and irrigation system, it is not intended to be limited to the details shown since various modifications and structural changes may be made without departing in any way from the spirit of the present invention.

What is claimed as new and desired to be protected by Letters Patent is set forth in the appended claims:

We claim:

1. An aspiration and irrigation system, in particular for performing surgical operations on an eye of a living being to maintain the intraocular pressure, comprising:
   a pressure unit for supplying a gaseous fluid to the eye via a first fluid passageway;
   infusion means for providing a liquid fluid, said infusion means including a first infusion bottle containing a liquid fluid at a fluid level in substantial alignment with the eye and a second infusion bottle arranged at a distance above and connected to said first infusion bottle via a dropper for allowing a flow of liquid fluid from said second infusion bottle to said first infusion bottle;
   irrigation means communicating with said first infusion bottle for conducting liquid fluid from said first infusion bottle to the eye via a second fluid passageway, said first infusion bottle communicating with said pressure unit via a third fluid passageway for introduction of gaseous fluid above the fluid level;
   valve means set in a fluid passageway between said irrigation means and said pressure unit on the one hand, and the eye on the other hand for selectively conducting the flow of fluid from said irrigation means and said pressure unit to the eye through said first and second fluid passageways; and,
   aspiration means for removing fluid and/or tissue from the eye.

2. An aspiration and irrigation system as defined in claim 1 wherein said valve is a three-way valve.

3. An aspiration and irrigation system as defined in claim 1, and further comprising a filter arranged in said first fluid passageway downstream of said pressure unit for sterilizing gaseous fluid supplied to the eye.

4. An aspiration and irrigation system as defined in claim 3 wherein said first fluid passageway and said third fluid passageway communicate with each other downstream of said filter to pressurize liquid fluid in said first infusion bottle with sterilized gaseous fluid.

5. An aspiration and irrigation system as defined in claim 1 wherein said first infusion bottle includes a float valve and a further valve in interaction with said float valve for allowing control of fluid flow from said first infusion bottle to said first infusion bottle in dependence on the liquid level in said first infusion bottle.

6. An aspiration and irrigation system as defined in claim 1 wherein said third fluid passageway enters said first infusion bottle above a maximum liquid level.

7. An aspiration and irrigation system as defined in claim 1, and further comprising a first pressure gage sensing a momentary intraocular pressure in the eye, said pressure unit including at least one gaseous fluid source, a control valve operatively connected to said gaseous fluid source, a second pressure gage sensing the pressure set at said control valve and a comparator operatively connected to said control valve and said first pressure gage for comparing the pressure determined by said first pressure gage with the pressure determined by said second pressure gage, thereby enabling a readjustment of the set pressure at said control valve.

8. An aspiration and irrigation system as defined in claim 1 wherein said irrigation means includes at least one interrupter element in form of a solenoid valve situated in said second fluid passageway for regulating the supply of sterilized liquid fluid to the eye.

9. An aspiration and irrigation system as defined in claim 8 wherein said interrupter element is provided with a squeeze member for interrupting the fluid flow in said second fluid passageway.

10. An aspiration and irrigation system as defined in claim 1 wherein said first, second and third fluid passageways are made of elastic material.

11. An aspiration and irrigation system as defined in claim 1 wherein said aspiration means includes a peristaltic pump for drawing fluid and/or tissue from the eye, a pressure gage for sensing the suction pressure of said peristaltic pump, a ventilation valve for discharging drawn gaseous fluid via a filter and control means operatively connected to said peristaltic pump for controlling the suction of said pump.

12. An aspiration and irrigation system as defined in claim 1, and further comprising a housing for accommodating said pressure unit, said irrigation means and said aspiration means.

13. An aspiration and irrigation system as defined in claim 12 wherein said housing is provided with a display panel in form of push-buttons and said pressure unit is provided with an adjustment knob, said push-buttons and said adjustment knob being provided for regulating the supply of fluid through said first, second and third passageway means.

14. An aspiration and irrigation system as defined in claim 13 wherein said display panel has at least one display field for indicating the momentary intraocular pressure so as to allow a pressure adjustment of the gaseous or liquid fluid by means of said pressure unit.

15. An aspiration and irrigation system for controlling the intraocular pressure of an eye, comprising:
first means for supplying a pressure gas to the eye;
infusion means for conducting a liquid fluid to the eye, said infusion means including a first infusion bottle at a level in substantial alignment with the eye and a second infusion bottle together with a dropper arranged at a distance above said first infusion bottle for supply of liquid fluid, with said first infusion bottle communicating with said first means for allowing a pressure adjustment of liquid fluid being conducted to the eye;
valve means set in a fluid passageway between said irrigation means and said pressure unit on the one hand, and the eye on the other hand for selectively controlling the flow of fluid from said first means and said infusion means to the eye; and
an aspiration means for removing liquid fluid from the eye.

* * * * *

UNITED STATES PATENT AND TRADEMARK OFFICE
CERTIFICATE OF CORRECTION

PATENT NO. : 5,360,398
DATED : November 1, 1994
INVENTOR(S) : Hans Grieshaber et al It is certified that error appears in the above-identified patent and that said Letters Patent is hereby corrected as shown below:

column 3, line 63 and column 4, lines 5 and 48, change "32" to --60--.

Column 7, lines 7 and 9, change "said first infusion bottle" to --said second infusion bottle--.

Signed and Sealed this

Twenty-first Day of March, 1995

*Attest:*

BRUCE LEHMAN

*Attesting Officer*      *Commissioner of Patents and Trademarks*